United States Patent
Gerbi et al.

(10) Patent No.: US 7,322,225 B2
(45) Date of Patent: Jan. 29, 2008

(54) ADHESION PROMOTION VACUUM MONITORING SYSTEM FOR PHOTO RESIST COATERS

(75) Inventors: Jason T. Gerbi, Roseville, CA (US); Mark J. Crabtree, Rocklin, CA (US)

(73) Assignee: NEC Electronics America, Inc., Santa Clara, CA (US)

( * ) Notice: Subject to any disclaimer, the term of this patent is extended or adjusted under 35 U.S.C. 154(b) by 110 days.

(21) Appl. No.: 10/983,456

(22) Filed: Nov. 8, 2004

(65) Prior Publication Data
US 2006/0096355 A1   May 11, 2006

(51) Int. Cl.
*G01N 23/00* (2006.01)
(52) U.S. Cl. .............. 73/37; 73/49.2; 702/51
(58) Field of Classification Search .............. 73/37, 73/49.2, 49.3; 702/51
See application file for complete search history.

(56) References Cited

U.S. PATENT DOCUMENTS

| | | | |
|---|---|---|---|
| 4,902,398 A * | 2/1990 | Homstad | 204/298.24 |
| 5,433,020 A * | 7/1995 | Leech, Jr. | 34/403 |
| 5,716,453 A | 2/1998 | Chen | |
| 6,156,125 A | 12/2000 | Harada | |
| 6,409,838 B1 * | 6/2002 | Sakai | 118/725 |
| 6,494,100 B1 * | 12/2002 | French, Jr. | 73/714 |

* cited by examiner

*Primary Examiner*—Daniel S. Larkin
(74) *Attorney, Agent, or Firm*—Campbell Stephenson LLP

(57) ABSTRACT

An apparatus and method for monitoring pressure within an adhesion promotion unit is provided. The apparatus in one embodiment includes a chamber configured to receive and heat a semiconductor wafer. A vacuum device is in fluid communication with a processing space within the chamber, wherein the vacuum device is configured to create a vacuum within the processing space. A vacuum monitor is also in fluid communication with the processing space, wherein the vacuum monitor generates a first electrical signal if gas pressure within the processing space is below a predetermined value. The apparatus may further include a processor in data communication with the vacuum monitor and the vacuum device. The vacuum device may generate a second electrical signal, and the processor generates a third electrical signal if the vacuum monitor fails to generate the first electrical signal within a predetermined amount of time after the vacuum device generates the second signal.

12 Claims, 2 Drawing Sheets

ADHESION PROMOTION VACUUM MONITORING SYSTEM FOR PHOTO RESIST COATERS

BACKGROUND OF THE INVENTION

Integrated circuits (IC's) are manufactured on semiconductor wafers using conventional photolithographic techniques. The process of manufacturing IC's involves many steps. One step includes depositing a photoresist layer on a semiconductor wafer surface. Photoresist layers are typically formed using a device called a photoresist coater. Photoresist coaters are well known in the art and typically spin coat photoresist material evenly onto the semiconductor wafer surface. The photoresist layer is subsequently exposed to light passing through a patterned reticle. Areas of the photoresist layer exposed to light are subsequently then removed using conventional development techniques to create a photoresist mask pattern. After formation of the photoresist mask pattern, a plasma etching operation can be applied to remove portions of the semiconductor layer exposed by the photoresist mask pattern.

The air surrounding the photoresist coater contains water molecules. As semiconductor wafers are loaded into the photoresist coater, dangling bonds of surface molecules (e.g., silicon, silicon dioxide, etc.) of the semiconductor wafer chemically attach to water molecules in the surrounding air. These attached water molecules may reduce the ability of the photoresist to adhere to the surface of the semiconductor wafer. Deposited photoresist often delaminates if the photoresist isn't sufficiently adhered to the surface of the semiconductor, particularly during the photoresist development step mentioned above. If the photoresist deposited on a semiconductor wafer delaminates, the semiconductor wafer must either be reworked or scrapped. Accordingly, it is important to remove all water molecules from the surface of the semiconductor wafer before photoresist is deposited thereon.

Semiconductor manufacturers often employ a photo resist adhesion promotion process to remove water molecules on the surface of semiconductor wafers before photoresist is deposited thereon. In this process, a semiconductor wafer is placed on a heating element (e.g., a hot plate) inside an airtight chamber of a device referred to as an adhesion promotion unit (APU). The heating unit heats the semiconductor to drive off unwanted water molecules (or other OH group molecules) attached to dangling bonds of surface molecules. A venturi vacuum device creates a vacuum which in turn removes air and other gases (e.g., water molecules driven off the surface of the semiconductor wafer) from the chamber as the semiconductor wafer is heated. Thereafter, hexamethyldisilizane (HMDS) vapor is introduced into the APU chamber. HMDS molecules attach to dangling bonds of wafer surface molecules so that the dangling bonds cannot later reattach to water molecules in the atmosphere when the wafer is removed from the APU chamber and moved to the photoresist coater. In essence, the adhesion promotion process results in a thin layer of HMDS on the surface of the semiconductor layer which in turn promotes adhesion of photoresist material.

If the APU is functioning correctly, the venturi vacuum device in conjunction with the heating element will drive off water molecules from the semiconductor wafer. APUs are equipped with pressure gages in fluid communication with the APU chamber. The pressure gages are visually checked once or twice a day by an operator to insure that a vacuum is created during the adhesion promotion process. APU components, unfortunately, are prone to undetected malfunctions that can prevent the creation of a vacuum which in turn prevents the removal of unwanted water molecules from the chamber. For example, an air leak may develop in the seal that makes the APU chamber airtight or in a conduit coupling the AiPU chamber and the venturi vacuum device, or the venturi vacuum device may fail. Any of these malfunctions or others may occur between visual checks of the APU pressure gage. If a sufficient vacuum is lacking within the chamber at the scheduled time the operator checks, all wafers previously processed since the last vacuum level check may be adversely affected and improperly processed prior to photoresist deposition. In other words, numerous wafers may have been processed with ineffective adhesion promotion before the condition of insufficient vacuum is discovered. Unfortunately, those improperly processed wafers will either require rework, or will be scrapped, depending on how far they have progressed before the low vacuum condition is discovered.

SUMMARY OF THE INVENTION

An apparatus and method for monitoring pressure within an adhesion promotion unit is provided. The apparatus in one embodiment includes a chamber configured to receive and heat a semiconductor wafer. A vacuum device is in fluid communication with a processing space within the chamber, wherein the vacuum device is configured to create a vacuum. A vacuum monitor is also in fluid communication with the processing space, wherein the vacuum monitor generates a first electrical signal if gas pressure within the processing space is below a predetermined value. The apparatus may further include a processor in data communication with the vacuum monitor and the vacuum device. The vacuum device may generate a second electrical signal, and the processor generates a third electrical signal if the vacuum monitor fails to generate the first electrical signal within a predetermined amount of time after the vacuum device generates the second signal.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DETAILED DESCRIPTION

Disclosed is an apparatus and method for monitoring gas pressure within an APU chamber. The present invention will be described with reference to the accompanying drawings. It is understood, however, that the present invention should not be limited to what is shown in the figures or by the description below.

Figure 1:
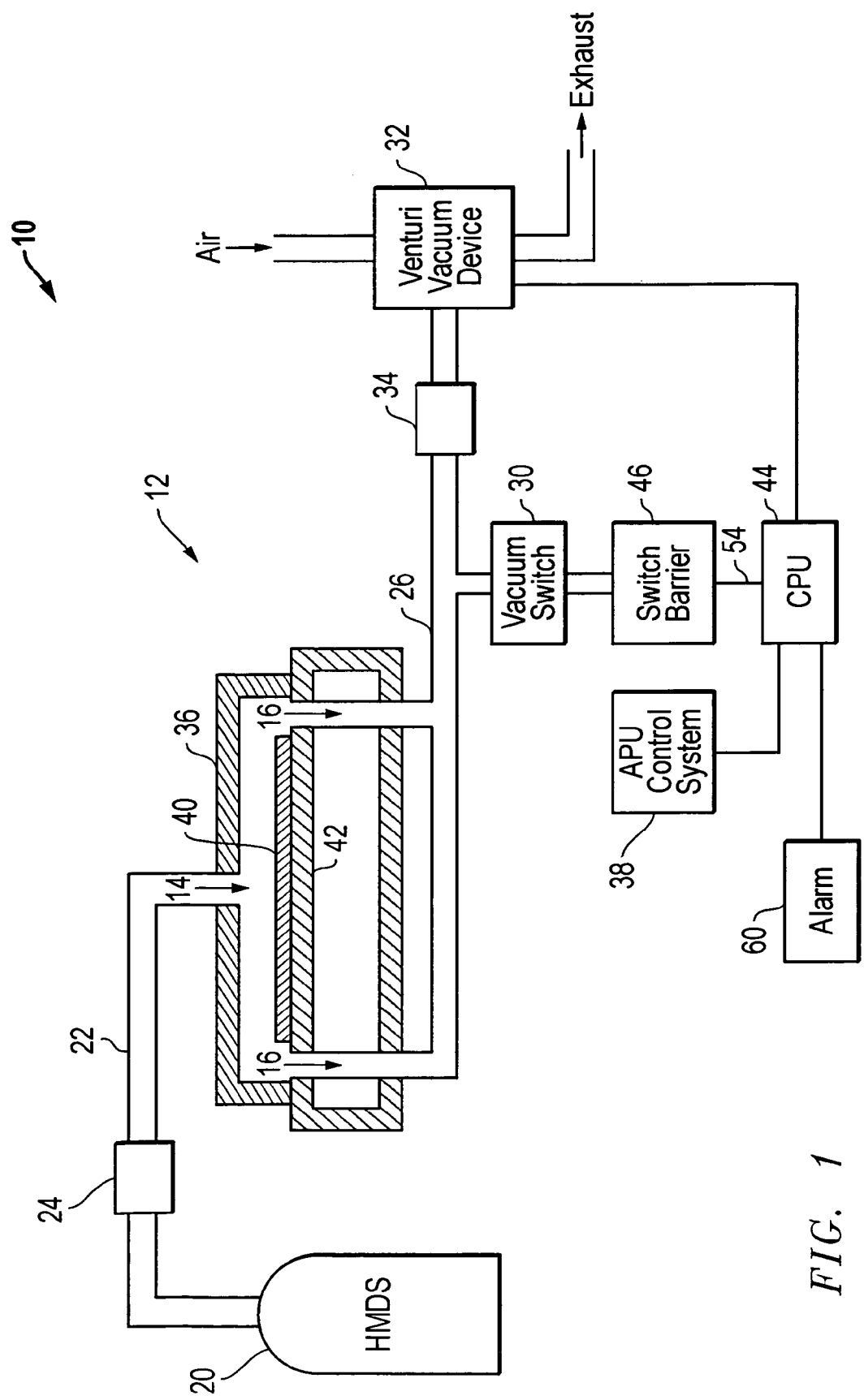
FIG. 1 illustrates a block diagram of an adhesion promotion unit (APU) employing one embodiment of the present invention.

FIG. 1 shows relevant components of an APU 10 employing one embodiment of the present invention. The APU 10 includes chamber 12 in which semiconductor wafers are processed for photo resist adhesion. Chamber 12 includes an inlet 14 and an outlet 16 through which gas or vapor may enter and exit chamber 12, respectively. The inlet 14 is coupled to an HMDS source 20 via a conduit 22 and an inlet valve 24. Inlet valve 24 is in fluid communication between the HMDS source 20 and wafer chamber 12. Inlet valve 24 passes HMDS vapor to chamber 12 depending upon whether the inlet valve is in the open or closed position. An outlet duct 26 connects outlet 16 to vacuum monitor 30 and a venturi vacuum device 32 via an outlet valve 34. Venturi vacuum device 32 when activated creates a vacuum which in turn removes gas including water vapor from the cavity or processing space of wafer chamber 12 when outlet valve 34 is in the open position. It is noted that venturi vacuum device 32 is one means for removing gas from the processing space within chamber 12, it being understood that other devices are contemplated for removing gas. It is also noted that the term vacuum is meant to mean a pressure within the processing space of chamber 12 that is lower than atmospheric pressure external to chamber 12.

Wafer chamber 12 includes a heating unit (e.g., a hot plate) 42 for receiving and heating a semiconductor wafer. Heating unit 42 drives off water molecules (or other OH group molecules) attached to dangling bonds of surface molecules on the semiconductor wafer being heated. FIG. 1 shows a wafer 40 inserted into wafer chamber 12 and resting on heating unit 42. Wafer chamber 12 also includes a moveable lid 36 that operates between the open and closed position. Lid 36 is shown in FIG. 1 in the closed position. However, in the open position, lid 36 allows access to the processing space of wafer chamber 12. Thus, when in the open position, lid 36 allows a semiconductor wafer to be inserted onto or removed from heating element 42. When in the closed position, lid 36 provides an airtight seal for the processing space of wafer chamber 12. Lid 36, heating unit 42 and other components are operatively controlled by an APU control system 38. In one embodiment, the APU control system 38 takes form in a computer system 38 that implements an adhesion promotion process in accordance with processor executable instructions stored in memory (not shown) as will be more fully described below.

Lastly, FIG. 1 shows a central processing unit (CPU) 44 in data communication with venturi vacuum device 32, vacuum monitor 30 via switch barrier 46, and APU control system 38. For purposes of explanation only, vacuum monitor 30 takes form in a vacuum switch, such as the W117V-3H-F11L-X vacuum switch manufactured by Whitman Controls Corporation of Bristol CT. Other vacuum monitors that perform the same or similar functions to a vacuum switch are contemplated for use in the present invention. Vacuum switch 30 is in fluid communication with the processing space of chamber 12 via duct 26 and monitors the gas pressure within the processing space of chamber 12. In general, vacuum switch 30 generates a signal when the gas pressure within the processing space is below a predetermined value thereby indicating that a sufficient vacuum exists in the processing space for successful implementation of the adhesion promotion process as will be more fully described below. Vacuum switch 30 may include a diaphragm biased by a spring such that when a vacuum is achieved, the diaphragm engages a contact in the switch and creates a conductive path for transmitting electrical current. Transmission of electrical current produces a signal indicative of a vacuum. A fitting may be needed to tie in the vacuum switch 30 to duct 26. CPU 44 receives the signal generated by vacuum switch 30 indirectly via switch barrier 46. Switch barrier is provided to limit power to switch 30 so that switch cannot generate a spark and ignite flammable HMDS. CPU 44 may be electrically isolated from APU control system 38, alarm 60, and/or venturi vacuum device 32 by opto-couplers.

Figure 2:
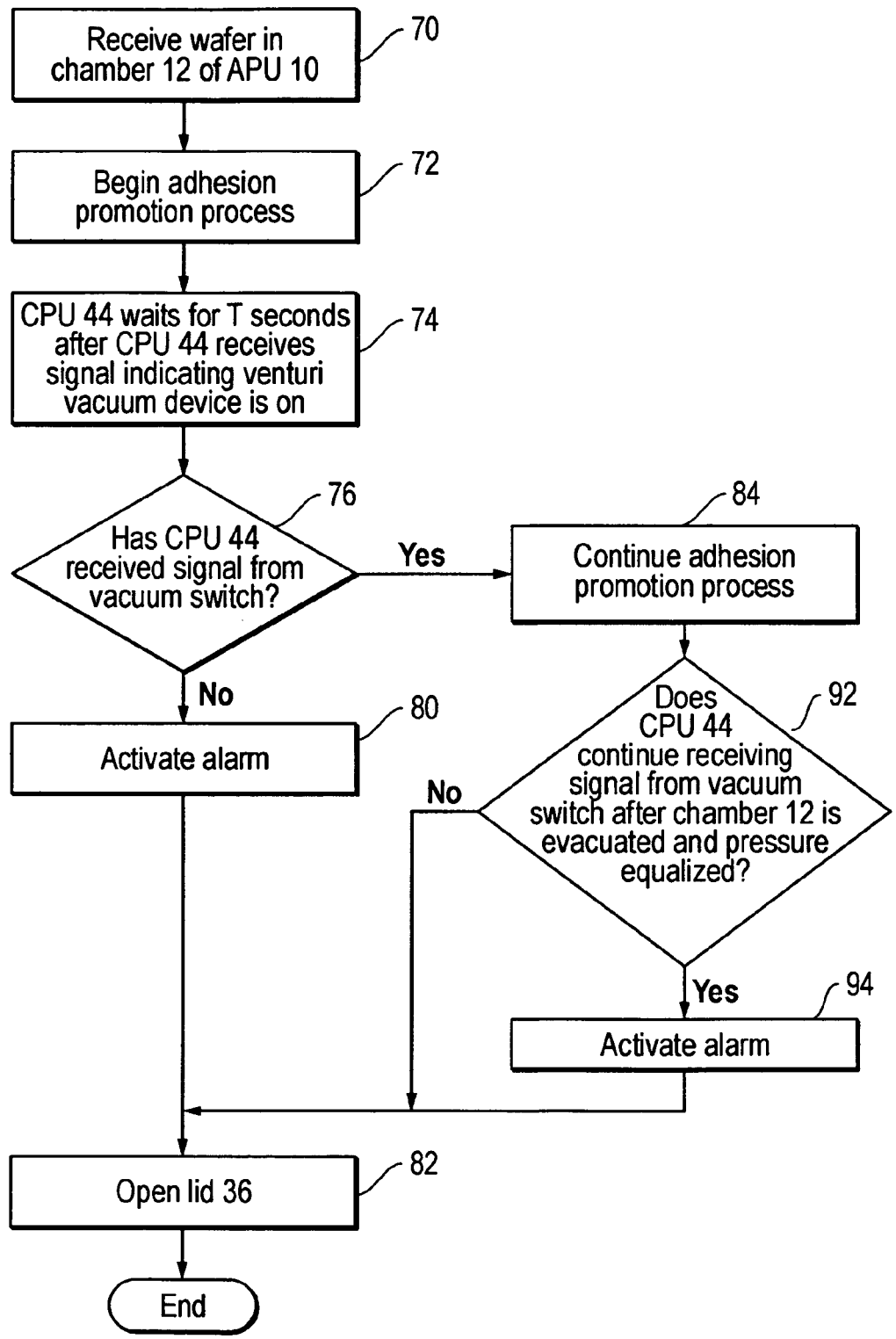
FIG. 2 is a flow chart illustrating relevant operational aspects of an adhesion promotion process employed in the APU of FIG. 1.

FIG. 2 is a flow chart illustrating relevant aspects of the adhesion promotion process implemented in APU 10. The process begins with step 70 when a semiconductor wafer (e.g., wafer 40) is received by heating element 42. It is noted that wafer 40 can be inserted into wafer chamber 12 and placed on heating element 42 using a robotic arm. Once the wafer is received, the APU control system 38 begins an adhesion promotion process as shown in step 72 in accordance with software instructions stored in memory. More particularly, in step 72 the APU control system 38 activates heating element 40 and a motor (not shown) that closes lid 36. Once the APU lid 36 is in the closed position, the APU control system 38 activates venturi vacuum device 32. It is noted that outlet valve 34 at this point is in the open position while inlet valve 24 is in the closed position. When activated, venturi vacuum device 32 generates and transmits a signal to CPU 44 indicating that the venturi vacuum device has started. As wafer 40 heats, water molecules attached to surface molecules of the wafer 40 are driven off and subsequently evacuated from chamber 12 by the vacuum created by venturi vacuum device 32, if venturi vacuum device 32 and other components of APU 10 are operating correctly.

CPU 44 executes a vacuum monitoring process in accordance with software instructions stored in memory (not shown). This process confirms that a proper vacuum exits in the processing space during the adhesion promotion process. In response to executing the instructions and in response to receiving the signal from venturi vacuum device 32, CPU 44 initiates an internal timer. After a certain amount of time T (e.g., T equals five seconds) has passed in step 74, CPU 44 in step 76 checks to see if it has received a signal from vacuum switch 30 via switch barrier 46 indicating that a predetermined vacuum level has been achieved within the processing space of wafer chamber 12. If after the predetermined time no signal has been received from vacuum switch 30, CPU 44 will activate alarm 60 as shown in step 80 and send a signal to APU control system 38 to terminate the adhesion promotion process. Alarm 60 may take form in a light emitting device (LED) and/or a device for generating an audio signal. In one embodiment, CPU 44 causes the LED to continuously output light as a visual signal indicating that a vacuum has not be achieved. The APU control system 38, on the other hand, deactivates heating element 42 and opens lid 36 in step 82 in response to receiving the adhesion promotion process termination signal from CPU 44.

If, however, CPU 44 receives the signal from vacuum switch 30 in step 76, water vapor driven off of wafer 40 is removed from the processing space of chamber 12 and the adhesion promotion process continues with step 84. More particularly, in step 84 APU control system 38 opens valve 24 and allows HMDS vapor to enter the processing space of chamber 12 from source 20. HMDS molecules bind with dangling bonds of the surface molecules such that the open receptors of the surface molecules of wafer 40 cannot later bind with water molecules when wafer 40 is removed from the processing space of chamber 12. After a predetermined time, the APU control system 38 closes inlet valve 24 such that no further HMDS vapor can enter wafer chamber 12. Venturi vacuum device 32 continues to to exhaust remaining HMDS vapor contained the processing space of wafer chamber 12. APU control system 38 then deactivates venturi vacuum device 32 and allows air to enter the processing space of chamber 12 in order to equalize the pressure within the processing space to the air pressure external to chamber 12.

In step 92, CPU 44 checks for the continued generation of signal from vacuum switch 30. If no signal is received by CPU 44 from vacuum switch 30 in step 92, APU control system 38 opens lid 36 in step 82 thereby indicating the end of the adhesion promotion process for wafer 40. If vacuum switch 30 is still generating a signal indicative of a vacuum in processing space of chamber 12, then in step 94 CPU 44 activates alarm 60 to indicate that vacuum switch 30 may be faulty before APU control system 38 opens lid 36 in step 82. In one embodiment, CPU 44 may activate the LED mentioned above so that it intermittently lights on and off thereby distinguishing the alarm generated in step 80. In step 94 CPU may also activate the audio alarm mentioned above.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

The invention claimed is:

1. An apparatus comprising:
    a chamber configured to receive and heat a semiconductor wafer;
    a vacuum device in fluid communication with a processing space within the chamber, wherein the vacuum device is configured to create a partial vacuum within the processing space;
    a vacuum monitor in fluid communication with the processing space, wherein the vacuum monitor generates a first electrical signal if gas pressure within the processing space is below a predetermined value; and
    a processor in data communication with the vacuum monitor and the vacuum device;
    wherein the vacuum device generates a second electrical signal; and
    wherein the processor generates a third electrical signal if the vacuum monitor fails to generate the first electrical signal within a predetermined amount of time after the vacuum device generates the second signal.

2. The apparatus of claim 1 wherein the vacuum device generates the second signal when the vacuum device is activated.

3. The apparatus of claim 1 further comprising an alarm, wherein the alarm is activated in response to the processor generating the third signal.

4. The apparatus of claim 1 wherein the vacuum monitor comprises a vacuum switch.

5. The apparatus of claim 1 wherein the vacuum device comprises a venturi vacuum device.

6. A method comprising:
    inputting a semiconductor wafer into a chamber;
    initiating a vacuum device in fluid communication with the chamber while the semiconductor wafer is in the chamber;
    heating the semiconductor wafer while the semiconductor wafer is in the chamber;
    generating a first electrical signal if gas pressure within the chamber is below a predetermined value as the semiconductor wafer is being heated;
    generating a second electrical signal when the vacuum device is initiated; and
    generating a third electrical signal if the first electrical signal is not generated within a predetermined amount of time after generation of the second electrical signal.

7. The method of claim 6 further comprising inputting hexamethyldisilizane HMDS vapor into the chamber unless the first electrical signal is generated.

8. The method of claim 6 further comprising generating an alarm in response to the generation of the third electrical signal.

9. An apparatus comprising:
    a chamber configured to receive and heat a semiconductor wafer;
    a vacuum device in fluid communication with a processing space within the chamber, wherein the vacuum device is configured to create a partial vacuum within the processing space;
    a means for generating a first electrical signal if a gas pressure of the processing space is below a predetermined value as the semiconductor wafer is being heated; and
    a processor in data communication with the means and the vacuum device;
    wherein vacuum device generates a second electrical signal; and
    wherein the processor generates a third electrical signal if the means fails to generate the first electrical signal within a predetermined amount of time after the vacuum device generates the second electrical signal.

10. The apparatus of claim 9 wherein the vacuum device generates the second signal when the vacuum device is activated.

11. The apparatus of claim 9 further comprising an alarm, wherein the alarm is activated in response to the processor generating the third signal.

12. A computer readable medium for storing instructions executable by a processor of a computer system, wherein the processor is in data communication with a vacuum monitor and a vacuum generator, wherein the vacuum monitor and vacuum generator are in fluid communication with a processing space of a chamber, wherein the chamber is configured to receive and heat a semiconductor wafer, wherein the processor performs a method in response to executing the instructions, the method comprising:
    generating a signal if the vacuum monitor fails to generate a first electrical signal within a predetermined amount of time after the vacuum device generates a second electrical signal;
    wherein the vacuum monitor generates the first electrical signal if gas pressure within the processing space is below a predetermined value; and
    wherein the vacuum generator generates the second electrical signal when the vacuum generator is activated.

* * * * *